United States Patent
Ciliberti et al.

(10) Patent No.: US 11,514,528 B1
(45) Date of Patent: Nov. 29, 2022

(54) PHARMACY BENEFIT MANAGEMENT MACHINE LEARNING SYSTEMS AND METHODS

(71) Applicant: Express Scripts Strategic Development, Inc., St. Louis, MO (US)

(72) Inventors: John Ciliberti, Sparta, NJ (US); Amit Gollapudi, Austin, TX (US); Richard Ball, Fair Lawn, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 820 days.

(21) Appl. No.: 16/446,825

(22) Filed: Jun. 20, 2019

(51) Int. Cl.
| | |
|---|---|
| *G06F 17/00* | (2019.01) |
| *G06Q 40/08* | (2012.01) |
| *G06K 9/62* | (2022.01) |
| *G06F 17/18* | (2006.01) |
| *G06N 20/00* | (2019.01) |
| *G16H 20/10* | (2018.01) |

(52) U.S. Cl.
CPC ............ *G06Q 40/08* (2013.01); *G06F 17/18* (2013.01); *G06K 9/6256* (2013.01); *G06K 9/6282* (2013.01); *G06N 20/00* (2019.01); *G16H 20/10* (2018.01)

(58) Field of Classification Search
CPC ........ G06Q 40/08; G16H 20/10; G06N 20/00; G06F 17/18; G06K 9/6256; G06K 9/6282
USPC ...................................................... 706/924
See application file for complete search history.

(56) References Cited

U.S. PATENT DOCUMENTS

| | | | |
|---|---|---|---|
| 8,140,421 B1 * | 3/2012 | Humphries | .......... G06Q 20/105 705/40 |
| 2004/0078234 A1 | 4/2004 | Tallal | |
| 2013/0253942 A1 | 9/2013 | Liu et al. | |
| 2013/0346496 A1 * | 12/2013 | Maarek | .................. G06Q 50/01 709/204 |
| 2014/0222349 A1 | 8/2014 | Higgins | |
| 2014/0278804 A1 * | 9/2014 | Lanxner | ............. G06Q 30/0206 705/7.35 |
| 2017/0019315 A1 | 1/2017 | Tapia | |
| 2017/0161758 A1 | 6/2017 | Towriss | |
| 2017/0185723 A1 | 6/2017 | McCallum et al. | |
| 2017/0316334 A1 | 11/2017 | Srivastava et al. | |
| 2018/0285969 A1 | 10/2018 | Busch et al. | |
| 2018/0322946 A1 | 11/2018 | Ika et al. | |
| 2019/0042887 A1 * | 2/2019 | Nguyen | ............... G06K 9/6257 |
| 2019/0080416 A1 | 3/2019 | Smith et al. | |
| 2019/0188760 A1 * | 6/2019 | Ekambaram | ....... G06Q 30/0283 |
| 2019/0304021 A1 * | 10/2019 | Rutherford | ............ G16H 10/60 |
| 2020/0364797 A1 * | 11/2020 | Halpern-Manners | ........................ G06N 5/025 |
| 2020/0410557 A1 * | 12/2020 | Liao | ........................ G06Q 30/02 |
| 2021/0256615 A1 * | 8/2021 | Hayward | ................. G06N 3/08 |

* cited by examiner

*Primary Examiner* — Jason T Edwards
(74) *Attorney, Agent, or Firm* — Stinson LLP

(57) ABSTRACT

A machine learning process for use with a pharmacy benefits management system. The machine learning process identifies a first predicted set of drug benefit claims impacted by a pricing error, reprices a sample of the first predicted set of drug benefit claims to adjust for the error, and trains a predictive model as a function of the repriced sample. Based on the trained model, the machine learning process predicts a second predicted set of drug benefit claims impacted by the error and initiates automatic repricing.

20 Claims, 12 Drawing Sheets

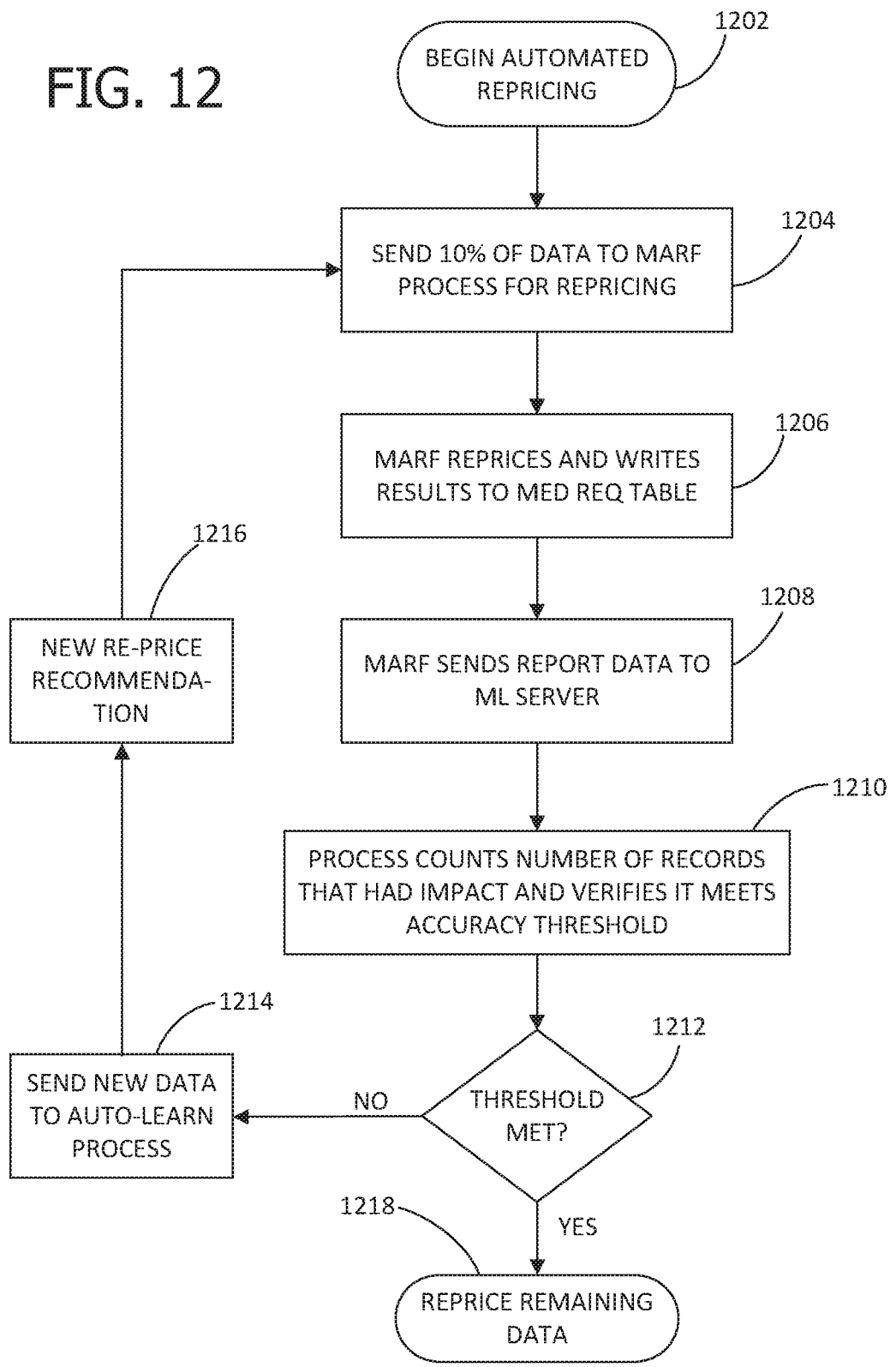

PHARMACY BENEFIT MANAGEMENT MACHINE LEARNING SYSTEMS AND METHODS

FIELD

Aspects of the present disclosure relate to machine learning in pharmacy benefit management and, in particular, automated machine learning systems and methods for predicting benefits claims that are impacted by a pricing error and repricing the impacted claims to implement large scale adjustments.

BACKGROUND

A pricing error on a claim by a pharmacy benefit manager (PBM) can result in overcharging a patient for a drug. The process for reporting, investigating, and remediating the impacted claim is slow and tedious, particularly if the error affects a large number of claims. It is very difficult to identify how many patients the error might have affected so that the PBM can make large scale adjustments. Conventional solutions often take weeks or months to remedy the impacted claims.

SUMMARY

In view of known problems associated with reporting, investigating, and remediating overcharging errors, systems and methods that can model the error and predict the impacted claims through machine learning are desired.

In an aspect, a pharmacy benefits management system includes a data store storing pricing data for drug benefit claims, a front end, a database service coupled to the front end, and a modeling processor coupled to the data store and to the database service. The front end generates an adjustment request associated with at least one drug benefit claim in response to user input. A memory stores computer-executable instructions that, when executed by the processor, configure the processor to retrieve the pricing data from the database for a selected drug benefit claim. In response to an adjustment request, the processor retrieves the pricing data associated with a known error in pricing of the selected drug benefit claim. The instructions further configure the processor to pre-process the retrieved pricing data for machine learning and generate a predictive model, which identifies a first predicted set of drug benefit claims impacted by the known error. In response to the adjustment request based on the retrieved pricing data, the instructions configure the processor to cause a sample of the first predicted set of drug benefit claims to be repriced in adjustment of the known error and train the predictive model as a function of the repriced sample to predict a second predicted set of drug benefit claims impacted by the known error. The modeling processor then stores the predictive model in a model repository of the database service.

In another aspect, a method includes generating, by a front end, an adjustment request in response to user input and retrieving, in response to the adjustment request, pricing data for a selected drug benefit claim from a data store. The data store stores pricing data for drug benefit claims and the adjustment request is associated with a known error in pricing of the selected drug benefit claim. The method also includes pre-processing the retrieved pricing data for machine learning and generating, by a modeling processor, a predictive model in response to the adjustment request based on the retrieved pricing data. The predictive model identifies a first predicted set of drug benefit claims impacted by the known error and the method further includes causing a sample of the first predicted set of drug benefit claims to be repriced in adjustment of the known error, training the predictive model as a function of the repriced sample to predict a second predicted set of drug benefit claims impacted by the known error, and storing the predictive model in a model repository.

In yet another aspect, a machine learning system includes a modeling processor and a memory. The modeling processing is coupled to a data store and a database service of a pharmacy benefits management system that stores pricing data for drug benefit claims. The memory stores a memory storing computer-executable instructions that, when executed by the processor, configure the processor to retrieve the pricing data from the data store for a selected drug benefit claim. The processor retrieves the data in response to an adjustment request generated by a front end of the pharmacy benefits management system and associated with a known error in pricing of the selected drug benefit claim. The processor is further configured to pre-process the retrieved pricing data for machine learning and generate a predictive model in response to the adjustment request based on the retrieved pricing data. The predictive model identifies a first predicted set of drug benefit claims impacted by the known error and the processor causes a sample of the first predicted set of drug benefit claims to be repriced in adjustment of the known error. The processor of the machine learning system is further configured to train the predictive model as a function of the repriced sample to predict a second predicted set of drug benefit claims impacted by the known error and store it in a model repository of the database service.

Other objects and features will be in part apparent and in part pointed out hereinafter.

BRIEF DESCRIPTION OF THE DRAWINGS

FIG. 12 is a flow diagram illustrating an example process for repricing claims in the machine learning process of FIG. 7.

Corresponding reference characters indicate corresponding parts throughout the drawings.

DETAILED DESCRIPTION

Figure 1:
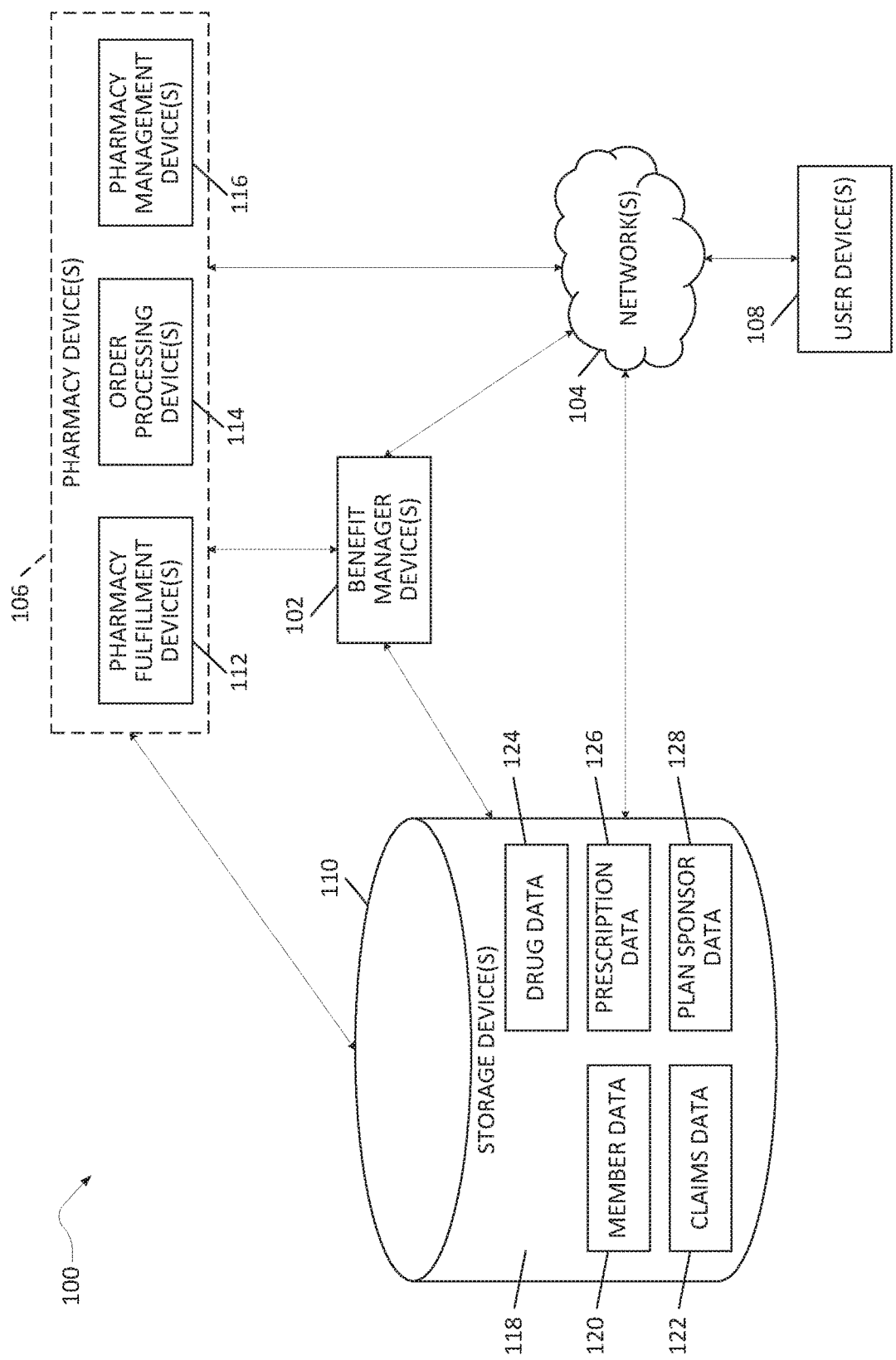
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, the term "feature selection" refers to the process of selecting a subset of relevant features (e.g., variables or predictors) that are used in the machine learning system to define data models. Feature selection may alternatively be described as variable selection, attribute selection, or variable subset selection. The feature selection process of the machine learning system described herein allows the prescription processing system to simplify models to make them easier to interpret, reduce the time to train the systems, reduce overfitting, enhance generalization, and avoid problems in dynamic optimization.

As used herein, the term "decision tree algorithm" refers to a supervised learning algorithm used for classification, regression and other tasks. The decision tree algorithm operates by constructing a training model visualized as a flowchart-like tree structure. The training model can predict class or value of target variables by learning decision rules inferred from prior data (training data).

As used herein, the term "naïve Bayesian algorithm" refers to a probabilistic classifier or regression that utilizes Bayes's theorem and applies naïve (or strong) independence assumptions between the features. Bayes's theorem can be stated as follows:

$$P(A \mid B) = \frac{P(B \mid A)P(A)}{P(B)},$$

where A and B are events and $P(B) \neq 0$. Like the random forest algorithm, the naïve Bayesian algorithm may be used for classification or regression.

The machine learning systems and methods described herein are configured to address known technological problems confronting computing systems and networks that process data sets, specifically the inability to quickly and efficiently process large scale adjustments to claims when a pricing error occurs. The machine learning systems and methods described are configured to address these known problems particularly as they relate to determining whether a known pricing error will impact a particular pharmacy benefit claim.

The machine learning systems and methods described overcome known deficiencies in previous technological approaches. Using previous approaches, the process of reporting, investigating, and remediating the impacted claim is slow and tedious, particularly if the error affects a large number of claims.

By contrast, the machine learning systems and methods provided allow the pharmacy benefits management system to quickly and automatically implement large scale adjustments. The machine learning systems and methods described can quickly react to an adjustment request, process a large volume of claims data based on a predictive model to identify and remediate impacted claims. As such these machine learning systems and methods solve a technological problem that cannot be otherwise resolved using known methods and technologies. In particular, the proposed approach of machine learning using a composite multi-algorithm approach to select a candidate model and train it to predict impacted claims is a significant technological improvement in the technological field of pharmacy benefits data sciences. Further, the proposed approach includes active re-training to ensure predictive accuracy. This approach also allows for re-training of the trained predictor as it is used. In this manner, the disclosed machine learning methods and systems prevent the data model and trained predictor from becoming static or stale and therefore possibly prone to error.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

Referring further to FIG. 1, the benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. In the embodiment of FIG. 1, the copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102 of FIG. 1) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

As shown in FIG. 1, benefit manager device 102 and pharmacy device 106 communicate with each other directly and/or over the network 104. Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

Referring further to FIG. 1, pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

Referring further to FIG. 1, order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 of FIG. 1 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 as shown in FIG. 1 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122. And in some implementations, the claims data 122 includes claims that identify the members with whom the claims are associated. Additionally or alternatively, the claims data 122 may include claims that have been de-identified (that is, associated with a unique identifier but not with a particular, identifiable member).

In an embodiment, the PBM system stores pricing data for drug benefit claims in the form of claims data 122 stored in storage device 110. In response to an adjustment, or repricing, request when a known pricing error occurs, the PBM system can retrieve the pricing data for a selected drug benefit claim associated with the error. As described in detail below, the PBM system generates a predictive model to identify a first predicted set of drug benefit claims impacted by the known error and, in response to the repricing request based on the retrieved pricing data, reprices a sample of the first predicted set of drug benefit claims to adjust for the known error. By training the predictive model as a function of the repriced sample, the PBM system is able to predict a second predicted set of drug benefit claims impacted by the known error.

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 of FIG. 1 includes information regarding the plan sponsors of the PBM. Examples of the plan sponsor data 128 include company name, company address, contact name, contact telephone number, contact e-mail address, etc.

Figure 2:
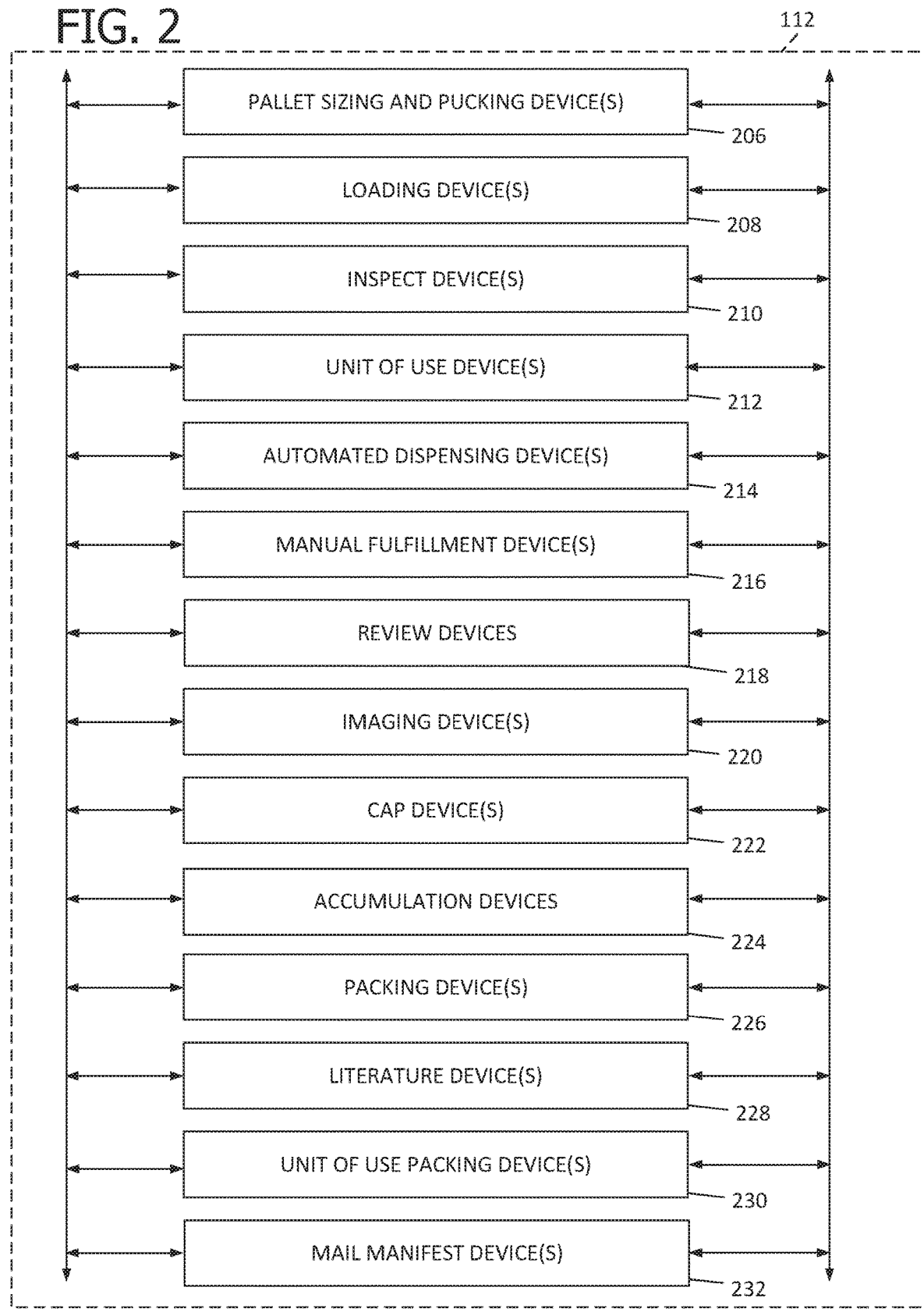
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

Referring further to FIG. 2, in some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 of FIG. 2 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 of FIG. 2 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

Referring further to FIG. 2, the manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 of FIG. 2 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
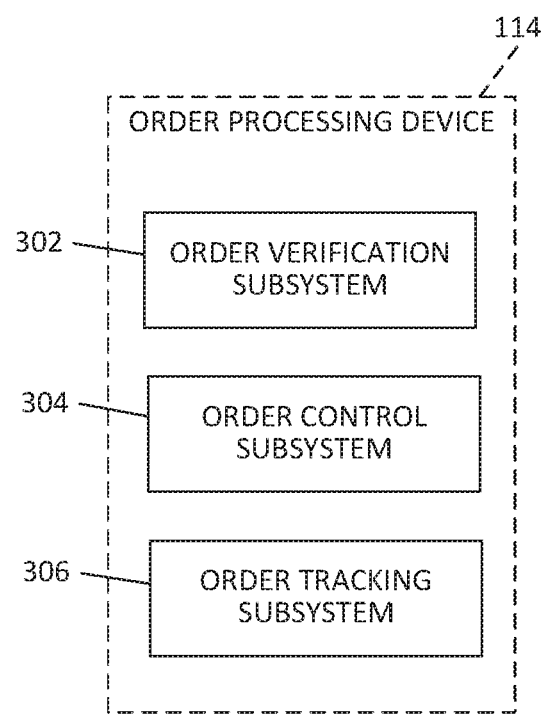
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

As shown in FIG. 3, the order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
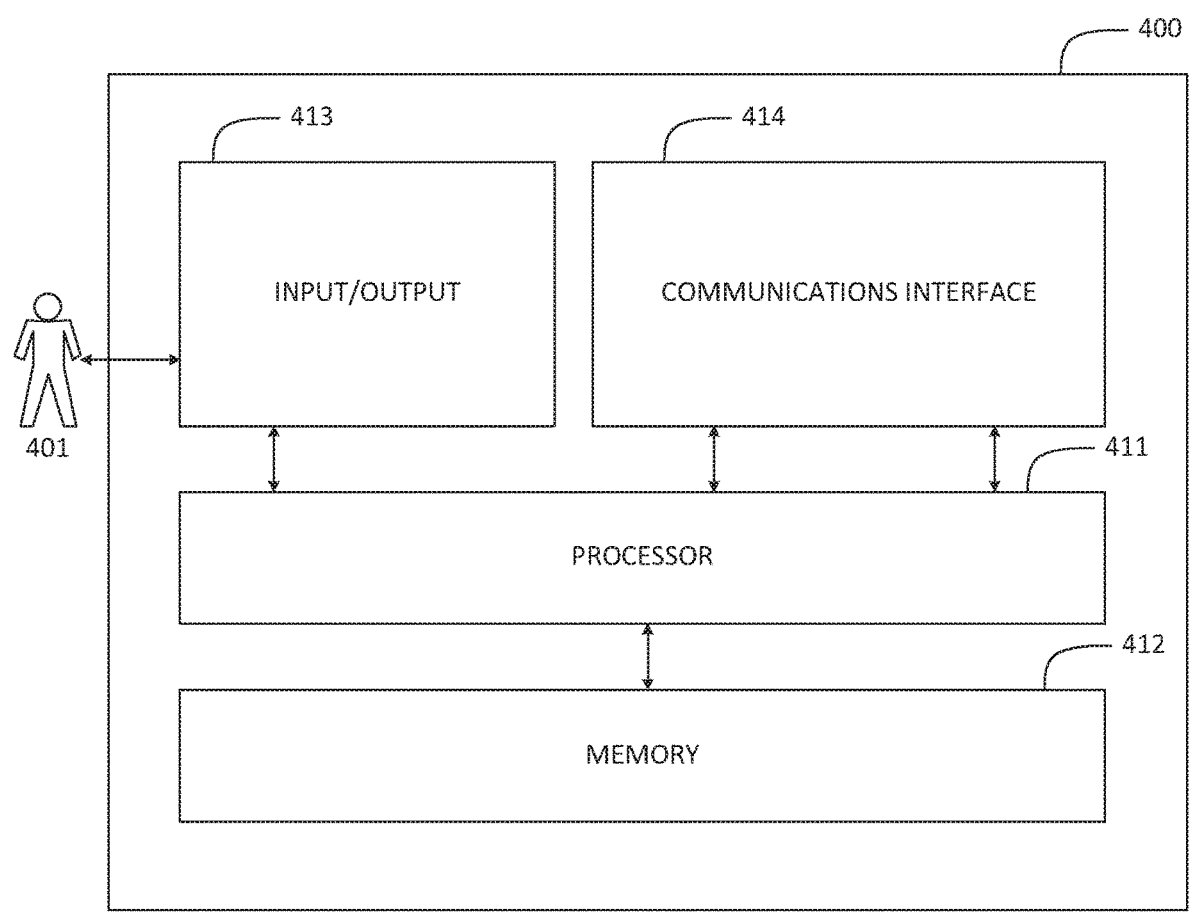
FIG. 4 is a functional block diagram of an example computing device that may be used in the system architecture of FIG. 1.

FIG. 4 is a functional block diagram of an example computing device 400 that may be used in the system architecture of FIG. 1. Specifically, the computing device 400 illustrates an exemplary configuration of a computing device such as prescription processing system, data warehouse, or other devices. Computing device 400 illustrates an exemplary configuration of a computing device operated by a user 401 in accordance with one embodiment of the present invention. Computing device 400 may include, but is not limited to, prescription processing system, data warehouse, other devices, other user systems, and other server systems. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of the machine learning methods for predicting whether a medical order requires PA described herein. In some variations, the characteristics of the described components may be more or less advanced, primitive, or non-functional.

In an exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

The computing device 400 also includes at least one input/output component 413 for receiving information from and providing information to the user 401. In some examples, input/output component 413 may be of limited functionality or non-functional as in the case of some wearable computing devices. In other examples, input/output component 413 is any component capable of conveying information to or receiving information from the user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from the user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

The computing device 400 of FIG. 4 may also include a communications interface 414, which is configurable to be communicatively coupled to a remote device such as a remote computing device, a remote server, or any other suitable system via the network 104. Communication interface 414 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

Figure 5:
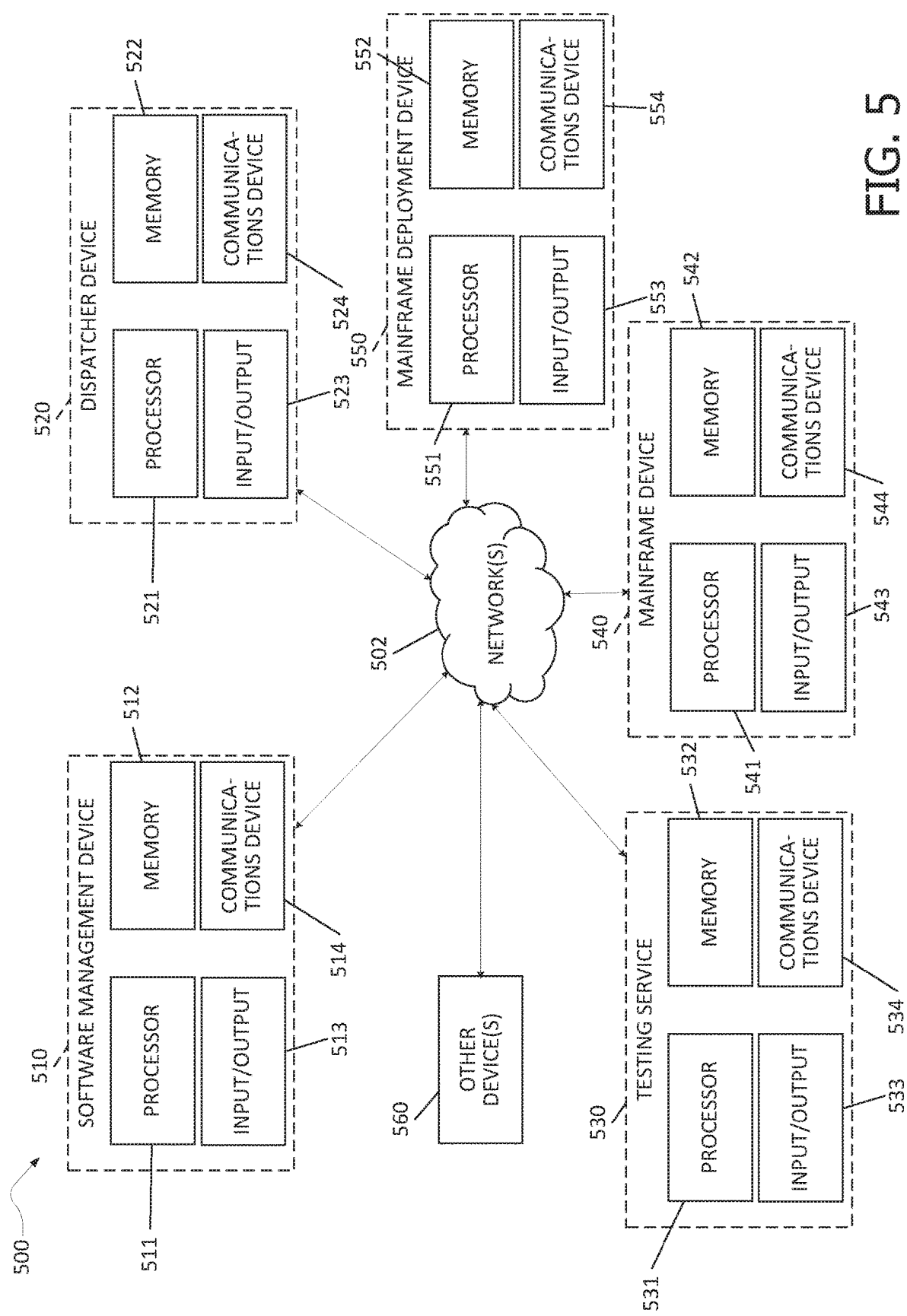
FIG. 5 is a functional block diagram of an example mainframe deployment system including a plurality of computing devices of FIG. 4.

FIG. 5 is a functional block diagram of a mainframe deployment system 500 including computing devices, such as computing devices 510, 520, 530, 540, 550, and 560 similar to the computing device 400 shown in FIG. 4. Software management device 510 is capable of providing software development management tools and capabilities to facilitate the processes described herein including, for example, maintaining and providing code sections that are evaluated and deployed according to the methods described herein. Software management device 510 includes a processor 511, a memory 512, an input/output 513, and a communications device 514. Dispatcher device 520 is configured to perform the dispatcher processes, and to coordinate the assignation of tasks, work, and activities to systems, programmers, or other entities. Dispatcher device 520 includes a processor 521, a memory 522, an input/output 523, and a communications device 524. Testing service 530 is configured to perform at least the pre-deployment test processes and the post-deployment test processes. Testing service includes a processor 531, a memory 532, an input/output 533, and a communications device 534.

Referring further to FIG. 5, the mainframe device 540 is configured to provide the applications and services that are the subject of the present disclosure, and it is the aim of aspects of the invention to use the mainframe deployment system 500 to provide stable, reliable deployments to mainframe device 540. Mainframe device 540 includes a processor 541, a memory 542, an input/output 543, and a communications device 544. In an embodiment, mainframe deployment device 550 is configured to facilitate or execute many of the processes described herein, and to coordinate the principal method of providing stable software deployments to mainframe device 540. Mainframe deployment device 550 includes a processor 551, a memory 552, an input/output 553, and a communications device 554. Other devices 560 may be designed in a manner similar to computing device 400 and similarly include processors, memories, input/outputs, and communication devices. Computing devices 510, 520, 530, 540, 550, and 560 are in networked communication via network 502.

Figure 6:
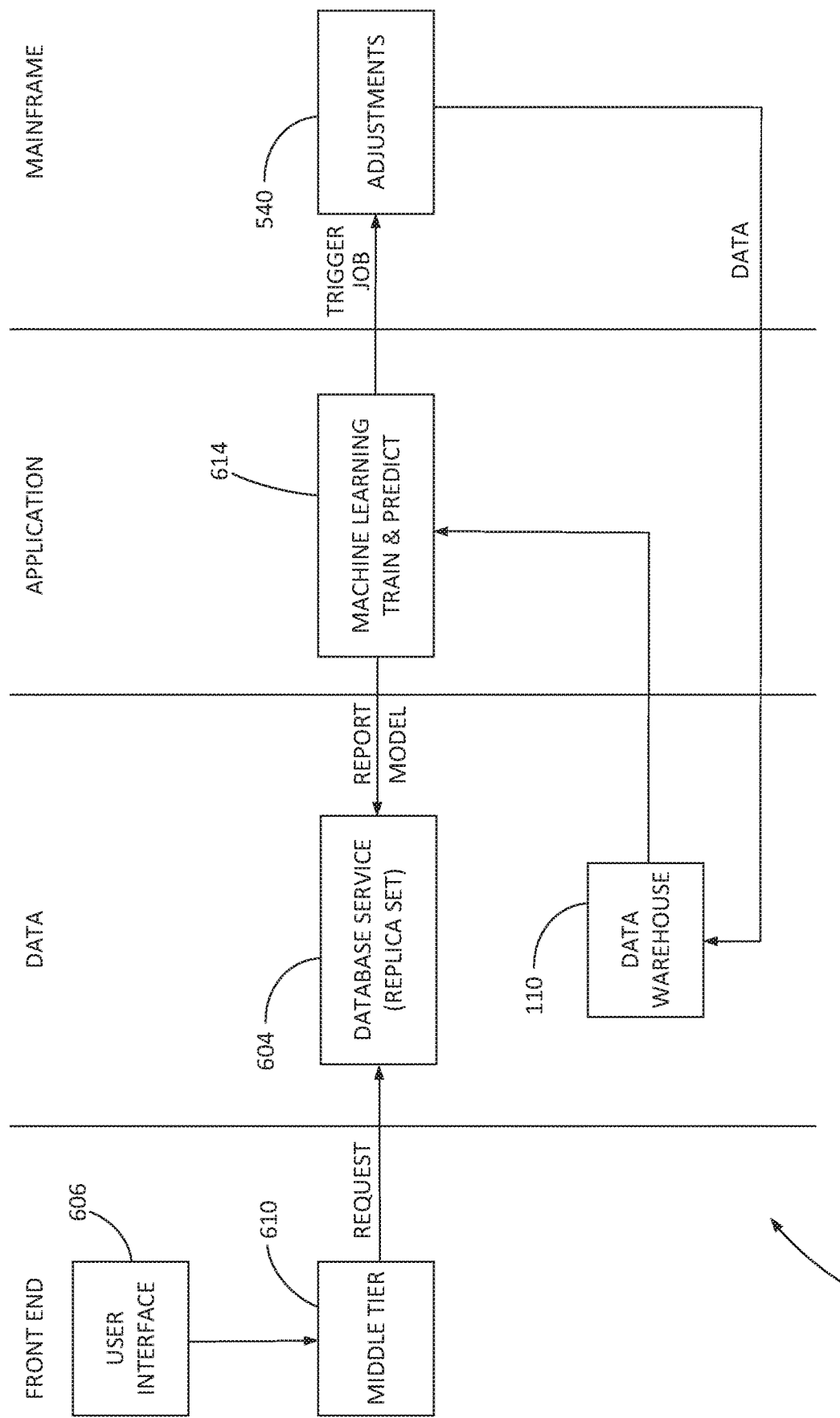
FIG. 6 is a functional block diagram of an example pharmacy benefits management machine learning production deployment according to an embodiment.

FIG. 6 is a functional block diagram of an example pharmacy benefits management machine learning production deployment according to an embodiment. As shown, an improved PBM system 602 houses pricing data for drug benefit claims in a data warehouse, data lake or other data store, embodied by storage device 110 storing claims data 122. In one embodiment, storage device 110 flattens the data for viewing and cooperates with a distributed database service 604 configured to store redundant replica sets, such as available from MongoDB, Inc. or the like.

A front end 606 implements a user interface for receiving a request to make an adjustment to a drug benefit claim because of a pricing error. In response to user input, the front end 606 sends the request to the database service 604 via a web service call from a middle tier 610. In an embodiment, the front end 606 includes a user interface built using a JavaScript library such as React, maintained by Facebook, and the middle tier 610 includes an application built on a Java platform such as Spring Boot, available from Pivotal Software, Inc. Both may be delivered via a platform such as Pivotal Cloud Foundry® from Pivotal Software, Inc.

A modeling processor 614 as shown in FIG. 6 executes an application programming interface (API) to select the request via database service 604 and begin preparing the pricing data stored in the storage device 110 for processing. In an embodiment, the modeling processor 614 includes computing device 400. In an alternative embodiment, modeling processor 614 includes mainframe device 540. The processor 614 implements one or more machine learning processes to predict impacted claims, reprice the impacted claims, and generate reports.

Referring further to FIG. 6, processor 614 executes a machine learning classifier to search candidate models from the pricing data stored in storage device 110. The processor 614 extracts a "chunk" of data (e.g., 100 GB), reads the records contained in the extracted chunk, and uses the stored model to predict which claims will have financial impact such that they require repricing. In an embodiment, a pricing error of even a fraction of a cent is considered to cause a financial impact. After training and selecting the best candidate model, processor 614 executing the classifier stores the selected model in database service 604. In this manner, database service 604 archives the machine learning models.

The storage device 110 cooperates with the training and prediction processes to deliver data analytics. In an embodiment, the system 602 employs Teradata data analytics from Teradata Corporation to implement the data warehouse of storage device 110. The mainframe device 540, in response to processor 614, executes an adjustments routine to perform repricing of the impacted claims. Once repricing has been approved, mainframe device 540 reprices a sample of the data (e.g., 10% of the 50,000 records), determines whether the number of records that had impact meets an accuracy threshold, and repeats the machine learning process executed by modeling processor 614 based on the repriced data, thus, improving the model.

In an embodiment, modeling processor 614 executes the machine learning training and prediction processes in two clusters, namely, a machine learning training cluster and a machine learning prediction cluster. The clusters each represent multiple applications clustered by a container orchestrations system such as an open source solution available from Kubernetes. In addition to applications, the clusters each include an engine (e.g., Docker "containerization" program available from Docker, Inc.) for deploying the applications with the container, a graphics processing unit (GPU) driver (e.g., CUDA® parallel computing platform available from NVIDIA Corporation), and graphics processing units.

As described above, PBM system 602 stores pricing data for drug benefit claims in a data lake or data warehouse (e.g., storage device 110). In an embodiment, the pricing data is arranged in columns of 3500 or more data features covering an enormous number of aspects of each claim. In response to a repricing request due to a known pricing error, processor 614 executes the prediction cluster to generate a predictive model and stores it in a model repository, such as database service 604. The training cluster retrieves pricing data for a selected drug benefit claim associated with the error from storage device 11 and identifies a first predicted set of drug benefit claims impacted by the known error. In response to the repricing request based on the retrieved pricing data, mainframe 540 reprices a sample of the first predicted set of drug benefit claims to adjust for the known error. A machine learning processor, or server, executes the training cluster, which uses the repriced sample to train the predictive model. In an embodiment, the machine learning processor includes modeling processor 614. This permits the prediction cluster of the PBM system 602 to predict a second predicted set of drug benefit claims impacted by the known error.

Figure 7:
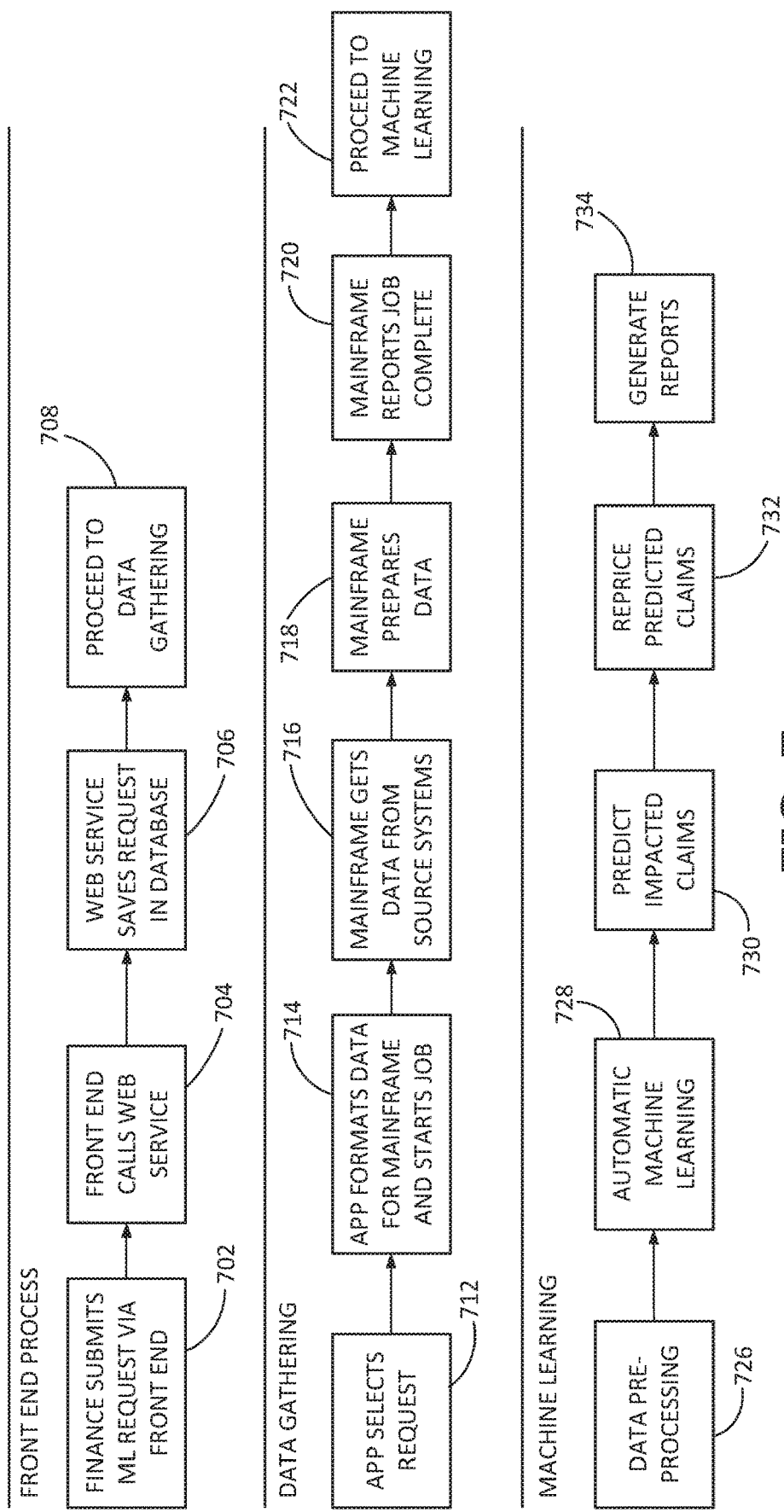
FIG. 7 is a flow diagram of an example process overview of a pharmacy benefits management machine learning system implementing the deployment of FIG. 6.

FIG. 7 is a flow diagram of an example pharmacy benefits management machine learning system implementing the deployment of FIG. 6. Specifically, FIG. 7 illustrates a machine learning repricing method in the form of a "swim lane" diagram. A front end process begins at 702 in which a user submits a machine learning ("ML") request via the user interface 606. At 704, the middle tier 610 initiates a web service call to transmit the request to database service 604 and saves it at 706. As indicated at 708, the flow proceeds to data gathering.

The machine learning server (e.g., modeling processor 614) executes an application to select the request at 712 and format the data at 714 for the mainframe 540. Mainframe 540 gets the data from source systems (e.g., storage device 110) at 716, prepares the data at 718, and reports the job as complete at 720. At 722, the flow proceeds to machine learning.

Referring further to FIG. 7, the machine learning operations begin at 726 with data pre-processing by the machine learning server (e.g., modeling processor 614). At 728, automatic machine learning trains the model so that it can predict impacted claims at 730, reprice the predicted claims at 732, and generate reports at 734.

Figure 8:
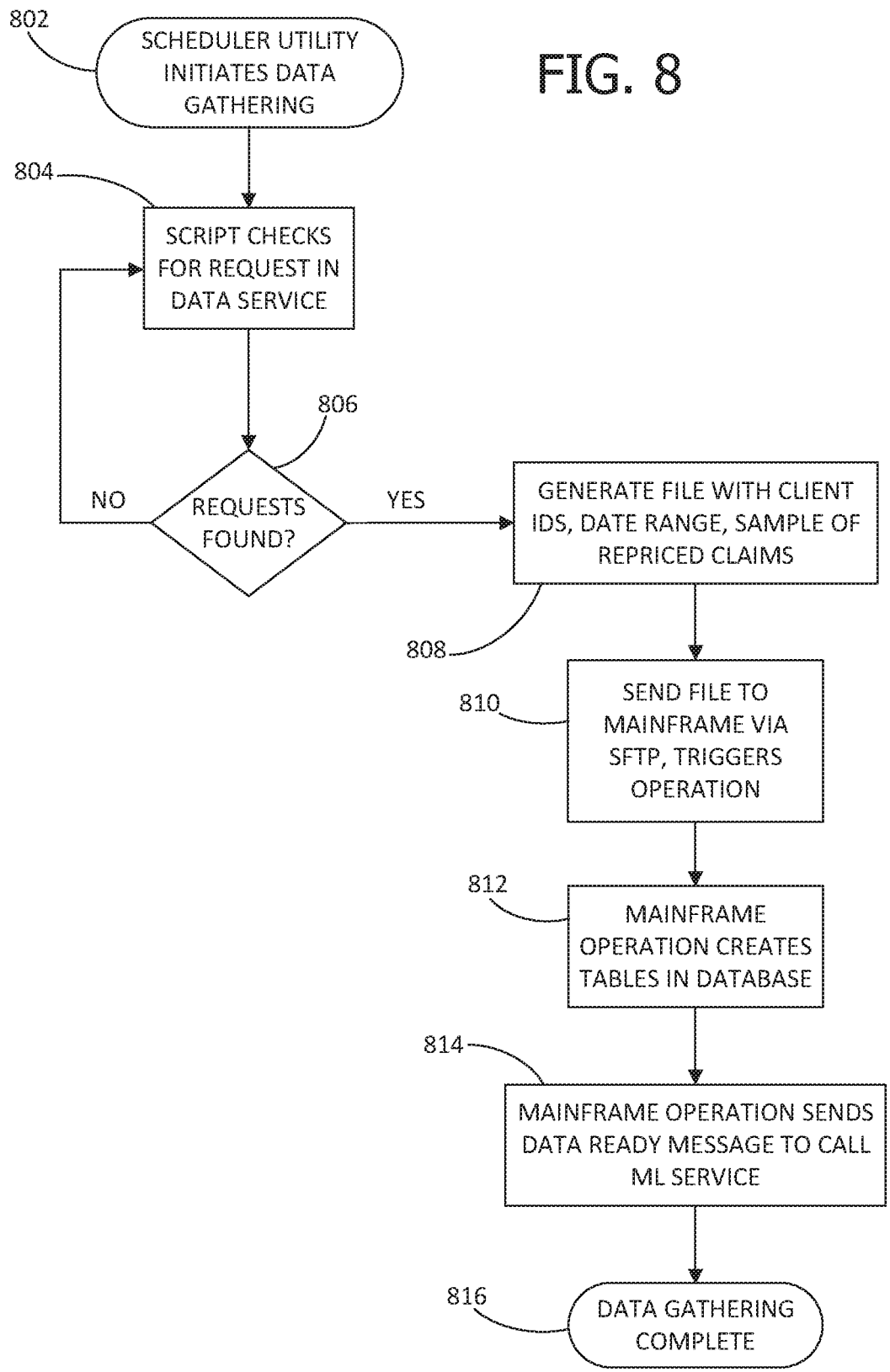
FIG. 8 is a flow diagram illustrating an example process for data gathering in the machine learning process of FIG. 7.

FIG. 8 is a flow diagram illustrating an example process for data gathering in the machine learning process of FIG. 7 at 712, 714, 716, 718, and 720. Beginning at 802, a scheduler utility (e.g., cron) kicks of the machine learning job on modeling processor 614. The processor 614 executes a script at 804 to check for the request stored in database service 604. If it is found at 806, the request triggers a job on mainframe 540. For instance, at 808 processor 614 generates a file containing client identifiers, a date range for the claims that might be impacted by the pricing error, and a sample of repriced claims for adjudication. At 810, modeling processor 614 sends the file to mainframe 540 via a secure file transfer and, at 812, mainframe 540 creates data tables in storage device 110 for processing. In an embodiment, the data tables include adjusted claims having financial impact and metadata describing the claims. The mainframe 540 then notifies processor 614 at 814 that the data is ready for training thus signaling completion of the data gathering stage at 816.

Figure 9:
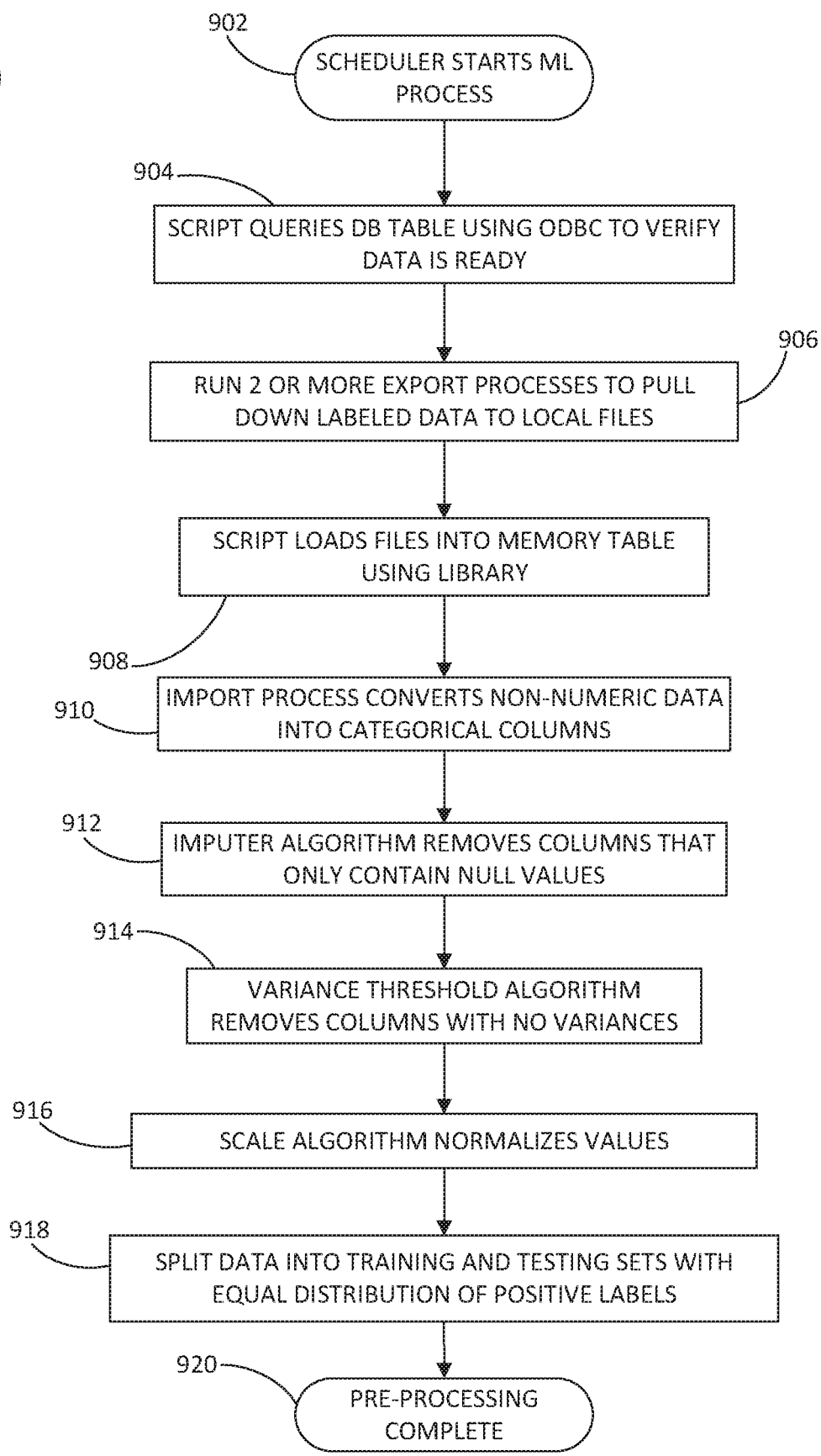
FIG. 9 is a flow diagram illustrating an example process for data pre-processing in the machine learning process of FIG. 7.

FIG. 9 is a flow diagram illustrating an example process for data pre-processing in the machine learning process of FIG. 7 at 724. Again, processor 614 executes a scheduler utility such as cron to begin the machine learning process at 902. The machine learning server (e.g., processor 614) executes a script at 904 to query the data table using, for example, an Open Database Connectivity (ODBC) application programming interface (API) to determine whether data is available for processing and to verify the data is ready run. At 906, processor 614 runs two or more export processes to pull down labeled data to local files and, at 908, processor 614 executes a script to load the files into memory. Processor 614 preferably extracts the data in chunks (e.g., one month of data) as a function of the available memory. In this embodiment, labeled data refers to the claims that were labeled during adjudication to be financially impacted by the pricing error. Using a library import process at 910, processor 614 converts non-numeric pricing data, such as dates, into categorical columns to provide numeric characterizations of data strings. Proceeding to 912 and 914, processor 614 executes feature reduction operations, such as executing an imputer algorithm to remove columns from the data tables that only contain null values and a variance threshold algorithm to remove columns from the data tables with no variances. The processor 614 performs a tunable scale algorithm at 916 to normalize the values. For example, suitable feature reduction and scaling algorithms are available from scikit-learn in Python®. Processor 614 then splits the data at 918 into training and testing sets. The sizes of the training and testing sets are configurable and, in an embodiment, the training and testing sets are configured to have equal distribution of positive labels. For example, the training set contains 60% of the data and the testing set contains 40% of the data or the training set contains 70% of the data and the testing set contains 30% of the data. This completes pre-processing at 920.

Figure 10:
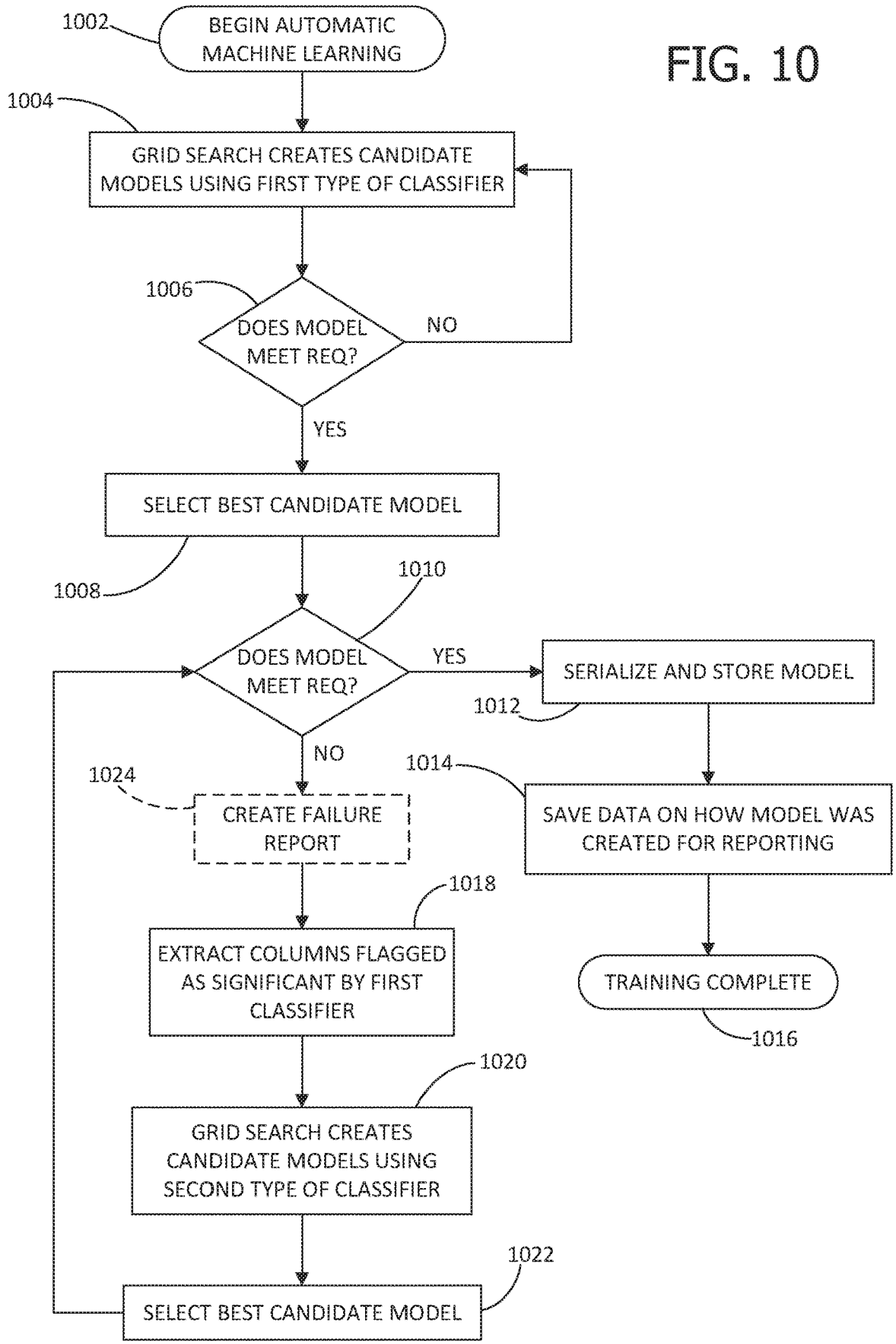
FIG. 10 is a flow diagram illustrating an example process for training the machine learning process of FIG. 7.

FIG. 10 is a flow diagram illustrating an example process for training the machine learning process of FIG. 7 at 726. Beginning the machine learning process at 1002, the machine learning processor (e.g., modeling processor 614) proceeds to 1004 to create candidate models. In an embodiment, processor 614 executes a grid search using a first type of classifier, such as a decision tree algorithm. For example, a suitable grid search and classifier is available from scikit-learn in Python®, which creates several hundreds of candidate models using a gradient boosted decision tree such as XGBoost and combines accuracy and performance with a boosted score to obtain a higher rate of positive classifications. If the selected candidate model does not meet a predetermined threshold of false positives at 1006, processor 614 preferably refines the model selection by repeating up to, for example, three times before selecting the best candidate model at 1008 (e.g., model is 90% accurate and has a recall rate for positive classifications greater than 95%). It is to be understood that the model preferably avoids false negatives. In other words, the preferred model will cause adjustments to false positives to avoid missing a true positive.

In an embodiment, each time the process repeats, processor 614 extracts the columns of data that the decision tree algorithm flagged as significant. If the selected candidate model meets the predetermined threshold of false positives at 1010, processor 614 serializes and stores the selected model in database service 604 at 1012 and also saves data on how the model was created in database service 604 at 1014 for reporting. This completes training of the model at 1016.

On the other hand, if the selected candidate model does not meet the predetermined threshold of false positives at 1010, processor 614 extracts the columns of data that the decision tree algorithm flagged as significant at 1018 and executes a grid search using a second type of classifier, such as a Gaussian naïve Bayes algorithm, at 1020 and selects the best candidate model at 1022. Returning to 1010, if the selected model fails to meet the predetermined requirements, processor 614 generates a failure report at 1024.

Figure 11:
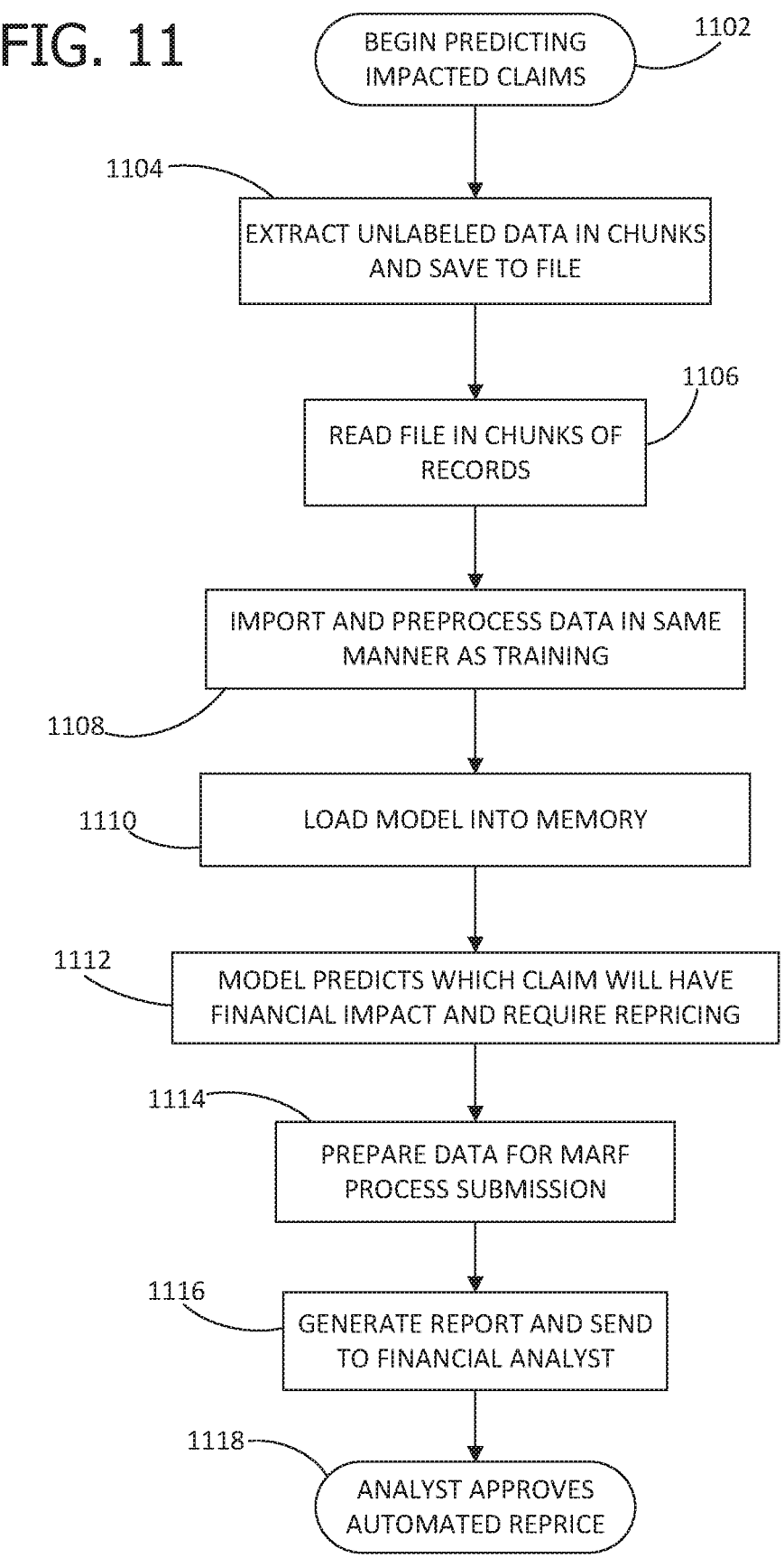
FIG. 11 is a flow diagram illustrating an example process for predicting impacted claims in the machine learning process of FIG. 7.

FIG. 11 is a flow diagram illustrating an example process for predicting impacted claims in the machine learning process of FIG. 7 at 728. Once training of the model is complete, processor 614 executes the machine learning process at 1102 to predict impacted claims. The processor 614 first extracts unlabeled data at 1104 in chunks for processing efficiency and saves the extracted data to a file. For example, a suitable chunk size is 100 GB. For smaller data sets, the entire data set is extracted in a single chunk. At 1106, processor 614 reads file in chunks designed to fit in the available memory (e.g., 50,000 records). Proceeding to 1108, the processor 614 imports the data for pre-processing in the same manner as occurred for training the model. The processor 614 pulls the selected model from database service 604 and loads it into the machine learning server's memory at 1110 for execution. The model predicts at 1112 which claims of the unlabeled data set will have financial impact and require repricing. The processor 614 prepares the data for MARF submission at 1114 to effect the repricing by mainframe 540 and generates a report for a financial analyst at 1116. At 1118, at the analyst's approval initiates automated repricing. As referred to herein, MARF is a mainframe reconciliation process for adjudicating and repricing claims based on eligibility on the date of a particular claim and the available benefits for the eligible claim.

FIG. 12 is a flow diagram illustrating an example process for repricing claims in the machine learning process of FIG. 7 at 730. Beginning with the analyst's approval to reprice at 1202, processor 614 sends a sample (e.g., 10%) of the data to mainframe 540 for automated repricing at 1204 in accordance with the MARF process. Testing the model in this manner based on a relatively small sample provides an opportunity to refine the model as needed before relying on it for large scale adjustments. The MARF process reprices the sample at 1206 and mainframe 540 writes the results back to storage device 110 at 1208 and reports to the machine learning server (e.g., processor 614). At 1210, the process counts the number of records that had a financial impact and verifies the number meets a predetermined accuracy threshold (e.g., an acceptable level of false positives). If the threshold is not met at 1212, the data returns to the machine learning process of FIG. 10 to improve the model so that it can generate a new repricing recommendation at 1216. On the other hand, if the threshold is met at 1212, the claims in the remaining data are repriced at 1218.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware, such as: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLU-ETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

Some or all hardware features of a module may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a module may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit or hardware encompasses a single processor circuit or microprocessor that executes some or all code from multiple modules. The term group processor circuit or hardware encompasses a processor circuit or microprocessor that, in combination with additional processor circuits or microprocessors, executes some or all code from one or more modules. References to multiple processor circuits encompass multiple processor circuits or microprocessors on discrete dies, multiple processor circuits or microprocessors on a single die, multiple cores of a single processor circuit or microprocessor, multiple threads of a single processor circuit or microprocessor, or a combination of the above.

The term shared memory circuit or hardware encompasses a single memory circuit or device that stores some or all code from multiple modules. The term group memory circuit or hardware encompasses a memory circuit or device that, in combination with other memories, stores some or all code from one or more modules.

The term memory circuit or hardware is a subset of the term computer-readable medium. The term computer-readable medium, as used herein, does not encompass transitory electrical or electromagnetic signals propagating through a medium (such as on a carrier wave). The term computer-readable medium is therefore be considered tangible and non-transitory. Non-limiting examples of a non-transitory computer-readable medium are nonvolatile memory circuits or devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Preferably, computer-executable instructions are stored in a memory, such as the hard disk drive, and executed by the computer. Advantageously, the computer processor has the capability to perform all operations (e.g., execute computer-executable instructions) in real-time.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the disclosure.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A pharmacy benefits management system comprising:
    a data store storing pricing data for a plurality of drug benefit claims;
    a front end executing on a processor of a benefit manager device, the front end receiving and responsive to user input for generating an adjustment request associated with at least one of the plurality of drug benefit claims;
    a database service executing on a processor of the benefit manager device and coupled to the front end, the database service comprising a model repository;
    a modeling processor coupled to the data store and to the database service; and
    a memory storing computer-executable instructions that, when executed by the modeling processor, configure the modeling processor for:
    retrieving, in response to the adjustment request, the pricing data from the data store for a selected drug benefit claim, wherein the adjustment request is associated with a known error in pricing of the selected drug benefit claim;
    pre-processing the retrieved pricing data for machine learning;
    executing a machine learning classifier to create one or more candidate models;
    training the candidate models based on a training set of the retrieved pricing data;
    selecting one of the trained candidate models that meets a predetermined accuracy threshold as a predictive model;
    executing the predictive model in response to the adjustment request based on a testing set of the retrieved pricing data, wherein the predictive model identifies a first predicted set of drug benefit claims impacted by the known error;
    causing a sample of the first predicted set of drug benefit claims to be repriced in adjustment of the known error;
    training the predictive model as a function of the repriced sample to predict a second predicted set of drug benefit claims impacted by the known error; and
    storing the predictive model in the model repository of the database service.

2. The system of claim 1, wherein the modeling processor is further configured for causing the second predicted set of drug benefit claims to be repriced in adjustment of the known error.

3. The system of claim 1, wherein the modeling processor is further configured for executing one or more machine learning algorithms to generate and train the candidate models.

4. The system of claim 3, wherein the one or more machine learning algorithms comprise at least one of a decision tree classifier and a probabilistic classifier.

5. The system of claim 1, wherein pre-processing the retrieved pricing data includes converting non-numeric pricing data into categorical columns of numeric characterizations.

6. The system of claim 5, wherein pre-processing the retrieved pricing data further includes executing one or more feature reduction operations to remove at least one of the columns containing a null value before generating the predictive model.

7. The system of claim 5, wherein pre-processing the retrieved pricing data further includes executing one or more feature reduction operations to remove at least one of the columns having a variance lower than a threshold.

8. The system of claim 1, wherein pre-processing the retrieved pricing data includes splitting the pricing data into the training set and the testing set.

9. The system of claim 1, wherein the modeling processor is further configured to select the sample of the first predicted set of drug benefit claims within a date range as a function of a date of the known error.

10. A method comprising:
    generating, by a front end, an adjustment request in response to user input;
    retrieving, in response to the adjustment request, pricing data for a selected drug benefit claim from a data store, wherein the data store stores pricing data for a plurality of drug benefit claims and wherein the adjustment request is associated with a known error in pricing of the selected drug benefit claim;
    pre-processing the retrieved pricing data for machine learning;
    executing, by a modeling processor, a machine learning classifier to create one or more candidate models;
    training the candidate models based on a training set of the retrieved pricing data;
    selecting one of the trained candidate models that meets a predetermined accuracy threshold as a predictive model;
    executing, by the modeling processor, the predictive model in response to the adjustment request based on a testing set of the retrieved pricing data, wherein the predictive model identifies a first predicted set of drug benefit claims impacted by the known error;
    causing a sample of the first predicted set of drug benefit claims to be repriced in adjustment of the known error;
    training the predictive model as a function of the repriced sample to predict a second predicted set of drug benefit claims impacted by the known error; and
    storing the predictive model in a model repository.

11. The method of claim 10, further comprising causing the second predicted set of drug benefit claims to be repriced in adjustment of the known error.

12. The method of claim 10, further comprising executing one or more machine learning algorithms to generate and train the predictive model.

13. The method of claim 12, wherein the one or more machine learning algorithms comprise at least one of a decision tree classifier and a probabilistic classifier.

14. The method of claim 10, wherein pre-processing the retrieved pricing data includes converting non-numeric pricing data into categorical columns of numeric characterizations.

15. The method of claim 14, wherein pre-processing the retrieved pricing data further includes executing one or more feature reduction operations to remove at least one of the columns containing a null value before generating the predictive model.

16. The method of claim 14, wherein pre-processing the retrieved pricing data further includes executing one or more feature reduction operations to remove at least one of the columns having a variance lower than a threshold.

17. The method of claim 10, wherein pre-processing the retrieved pricing data includes splitting the pricing data into a training set and a testing set.

18. The method of claim 10, wherein the modeling processor is further configured to select the sample of the first predicted set of drug benefit claims within a date range as a function of a date of the known error.

19. A machine learning system comprising:
   a modeling processor coupled to a data store and a database service of a pharmacy benefits management system, the data store storing pricing data for a plurality of drug benefit claims, the database service comprising a model repository; and
   a memory storing computer-executable instructions that, when executed by the modeling processor, configure the modeling processor for:
   retrieving, in response to an adjustment request, the pricing data from the data store for a selected drug benefit claim, wherein the adjustment request is generated by a front end of the pharmacy benefits management system and is associated with a known error in pricing of the selected drug benefit claim;
   pre-processing the retrieved pricing data for machine learning;
   executing a machine learning classifier to create one or more candidate models;
   training the candidate models based on a training set of the retrieved pricing data;
   selecting one of the trained candidate models that meets a predetermined accuracy threshold as a predictive model;
   executing the predictive model in response to the adjustment request based on a testing set of the retrieved pricing data, wherein the predictive model identifies a first predicted set of drug benefit claims impacted by the known error;
   causing a sample of the first predicted set of drug benefit claims to be repriced in adjustment of the known error;
   training the predictive model as a function of the repriced sample to predict a second predicted set of drug benefit claims impacted by the known error; and
   storing the predictive model in the model repository of the database service.

20. The system of claim 19, wherein pre-processing the retrieved pricing data includes at least one of: converting non-numeric pricing data into categorical columns of numeric characterizations; executing one or more feature reduction operations to remove at least one of the columns containing a null value before generating the predictive model; executing one or more feature reduction operations to remove at least one of the columns having a variance lower than a threshold; and splitting the pricing data into a training set and a testing set.

* * * * *